(12) United States Patent
Jacobs et al.

(10) Patent No.: US 8,246,574 B2
(45) Date of Patent: Aug. 21, 2012

(54) SUPPORT CATHETER

(75) Inventors: James M. Jacobs, Mountain View, CA (US); Randolf von Oepen, Los Altos Hills, CA (US); Richard Newhauser, Redwood City, CA (US); Travis Yribarren, Coarsegold, CA (US)

(73) Assignee: Abbott Laboratories, Abbott Park, IL (US)

( * ) Notice: Subject to any disclaimer, the term of this patent is extended or adjusted under 35 U.S.C. 154(b) by 562 days.

(21) Appl. No.: 11/738,368

(22) Filed: Apr. 20, 2007

(65) Prior Publication Data

US 2007/0270779 A1 Nov. 22, 2007

Related U.S. Application Data

(60) Provisional application No. 60/793,781, filed on Apr. 21, 2006.

(51) Int. Cl.
*A61M 31/00* (2006.01)
*A61M 29/00* (2006.01)
*A61M 5/178* (2006.01)
*A61M 1/00* (2006.01)
*A61B 5/00* (2006.01)
*A61F 11/00* (2006.01)

(52) U.S. Cl. ............... 604/95.01; 604/322; 604/164.13; 604/171; 604/96.01; 600/585; 606/108; 606/194

(58) Field of Classification Search ............. 604/322, 604/164.13, 174, 179, 180, 171, 175, 247, 604/27, 28, 43, 103.01, 164.04, 95.01, 96.01, 604/8; 600/585, 573, 575, 580; 606/194, 606/108, 172, 200

See application file for complete search history.

(56) References Cited

U.S. PATENT DOCUMENTS

| | | | |
|---|---|---|---|
| 4,405,313 A | 9/1983 | Sisley et al. | |
| 4,624,381 A | 11/1986 | Freidrich | |
| 4,832,681 A * | 5/1989 | Lenck | 600/34 |
| 4,921,479 A | 5/1990 | Grayzel | |
| 5,057,092 A | 10/1991 | Webster, Jr. | |
| 5,139,496 A | 8/1992 | Hed | |
| 5,180,366 A | 1/1993 | Woods | |
| 5,195,978 A | 3/1993 | Schiffer | |
| 5,250,069 A | 10/1993 | Nobuyoshi et al. | |
| 5,320,605 A | 6/1994 | Sahota | |

(Continued)

FOREIGN PATENT DOCUMENTS

EP 0 279 959 8/1988

(Continued)

OTHER PUBLICATIONS

U.S. Appl. No. 11/738,384, filed Apr. 20, 2007, Von Oepen.

(Continued)

*Primary Examiner* — Nicholas Lucchesi
*Assistant Examiner* — Ian Holloway
(74) *Attorney, Agent, or Firm* — Workman Nydegger; Jonathan D. Feuchtwang (57) ABSTRACT

A support catheter that can be used to aid positioning of a guidewire and other medical devices. The support catheter includes a catheter body having a length, and a supporting structure formed or disposed in or on the catheter body. The catheter support structure, whether alone or in combination with the other portions of the support catheter, provides flexibility, stiffness, and torqueability to the support catheter.

19 Claims, 4 Drawing Sheets

U.S. PATENT DOCUMENTS

| | | | |
|---|---|---|---|
| 5,324,255 A | 6/1994 | Passafaro et al. | |
| 5,378,237 A | 1/1995 | Boussignac et al. | |
| 5,380,273 A | 1/1995 | Dubrul et al. | |
| 5,385,563 A | 1/1995 | Gross | |
| 5,405,380 A | 4/1995 | Gianotti et al. | |
| 5,423,773 A * | 6/1995 | Jimenez | 604/526 |
| 5,437,288 A * | 8/1995 | Schwartz et al. | 600/585 |
| 5,443,454 A | 8/1995 | Tanade et al. | |
| 5,454,795 A * | 10/1995 | Samson | 604/526 |
| 5,460,608 A | 10/1995 | Lodin et al. | |
| 5,507,751 A * | 4/1996 | Goode et al. | 606/108 |
| 5,647,846 A * | 7/1997 | Berg et al. | 604/93.01 |
| 5,662,622 A * | 9/1997 | Gore et al. | 604/526 |
| 5,702,439 A | 12/1997 | Keith et al. | |
| 5,709,658 A | 1/1998 | Sirhan et al. | |
| 5,720,735 A | 2/1998 | Dorros | 604/284 |
| 5,855,563 A | 1/1999 | Kaplan et al. | |
| 5,906,606 A | 5/1999 | Chee et al. | |
| 5,951,517 A | 9/1999 | Lampropoulos et al. | |
| 6,017,324 A | 1/2000 | Tu et al. | |
| 6,022,309 A | 2/2000 | Celliers et al. | |
| 6,152,909 A | 11/2000 | Bagaoisan et al. | |
| 6,210,393 B1 | 4/2001 | Brisken | |
| 6,210,404 B1 | 4/2001 | Shadduck | |
| 6,217,503 B1 | 4/2001 | Weinberger et al. | |
| 6,221,100 B1 | 4/2001 | Strecker | |
| 6,241,744 B1 | 6/2001 | Imran et al. | |
| 6,261,273 B1 | 7/2001 | Ruiz | |
| 6,299,595 B1 | 10/2001 | Dutta et al. | |
| 6,327,505 B1 | 12/2001 | Medhkour et al. | |
| 6,398,772 B1 | 6/2002 | Bond et al. | |
| 6,398,791 B1 | 6/2002 | Que et al. | |
| 6,416,740 B1 | 7/2002 | Unger | |
| 6,440,161 B1 | 8/2002 | Madrid et al. | |
| 6,461,383 B1 | 10/2002 | Gesswein et al. | |
| 6,482,218 B1 | 11/2002 | Tran | |
| 6,579,246 B2 | 6/2003 | Jacobsen et al. | 600/585 |
| 6,582,390 B1 | 6/2003 | Sanderson | |
| 6,629,952 B1 | 10/2003 | Chien et al. | |
| 6,652,508 B2 * | 11/2003 | Griffin et al. | 604/526 |
| 6,679,879 B2 | 1/2004 | Shadduck | |
| 6,682,502 B2 | 1/2004 | Bond et al. | |
| 6,790,170 B2 | 9/2004 | Moody et al. | |
| 6,849,077 B2 | 2/2005 | Ricci | |
| 6,869,416 B2 | 3/2005 | Windheuser et al. | |
| 6,942,680 B2 | 9/2005 | Grayzel et al. | |
| 6,962,604 B2 | 11/2005 | Hijlkema | |
| 7,044,933 B2 | 5/2006 | VanDiver et al. | |
| 7,329,223 B1 | 2/2008 | Ainsworth et al. | |
| 7,344,528 B1 | 3/2008 | Tu et al. | |
| 7,789,906 B2 | 9/2010 | Blank | |
| 2001/0008976 A1 | 7/2001 | Wang | |
| 2001/0031243 A1 | 10/2001 | Unger | |
| 2002/0022831 A1 | 2/2002 | O'Connor et al. | |
| 2002/0072710 A1 | 6/2002 | Stewart et al. | |
| 2002/0107473 A1 | 8/2002 | Bond et al. | |
| 2002/0123716 A1 | 9/2002 | VanDiver et al. | |
| 2002/0123738 A1 * | 9/2002 | Jansen et al. | 604/526 |
| 2003/0009157 A1 | 1/2003 | Levine et al. | |
| 2003/0055377 A1 | 3/2003 | Sirhan et al. | |
| 2003/0069522 A1 * | 4/2003 | Jacobsen et al. | 600/585 |
| 2003/0135261 A1 | 7/2003 | Kugler et al. | |
| 2003/0191449 A1 | 10/2003 | Nash et al. | |
| 2004/0044350 A1 | 3/2004 | Martin et al. | |
| 2004/0054322 A1 | 3/2004 | Vargas | |
| 2004/0054347 A1 | 3/2004 | Zadno-Azizi et al. | |
| 2004/0093044 A1 | 5/2004 | Rychnovsky et al. | |
| 2004/0098021 A1 | 5/2004 | Laguna | |
| 2004/0102821 A1 | 5/2004 | Kawata et al. | |
| 2004/0103516 A1 | 6/2004 | Bolduc et al. | |
| 2004/0220473 A1 | 11/2004 | Lualdi | |
| 2004/0225278 A1 | 11/2004 | Poole et al. | |
| 2004/0230204 A1 | 11/2004 | Wortley et al. | |
| 2005/0004522 A1 | 1/2005 | Katoh et al. | |
| 2005/0021004 A1 * | 1/2005 | Cully et al. | 604/528 |
| 2005/0182371 A1 | 8/2005 | Wagner et al. | |
| 2005/0209582 A1 | 9/2005 | Quinn et al. | |
| 2006/0085023 A1 | 4/2006 | Davies, Jr. et al. | |
| 2006/0190022 A1 | 8/2006 | Beyar et al. | |
| 2007/0060880 A1 | 3/2007 | Gregorich et al. | |
| 2007/0250149 A1 | 10/2007 | Von Oepen | |
| 2007/0270779 A1 | 11/2007 | Jacobs et al. | |
| 2007/0293821 A1 | 12/2007 | Yribarren | |
| 2007/0293846 A1 | 12/2007 | Von Oepen | |
| 2007/0299392 A1 | 12/2007 | Beyar et al. | |
| 2008/0058722 A1 | 3/2008 | Von Oepen | |
| 2008/0065014 A1 | 3/2008 | Von Oepen | |

FOREIGN PATENT DOCUMENTS

| | | |
|---|---|---|
| EP | 0 596 635 | 5/1994 |
| EP | 0 916 359 | 5/1999 |
| EP | 1 475 120 | 11/2004 |
| EP | 1 607 119 | 12/2005 |
| GB | 2 143 920 | 2/1985 |
| WO | WO 88/08727 | 11/1988 |
| WO | WO 93/06780 | 4/1993 |
| WO | WO 96/07448 | 3/1996 |
| WO | WO 96/39205 | 12/1996 |
| WO | WO 97/23158 | 7/1997 |
| WO | WO 97/39690 | 10/1997 |
| WO | WO 99/15070 | 4/1999 |
| WO | WO 99/17826 | 4/1999 |
| WO | WO 99/21600 | 5/1999 |
| WO | WO 99/64098 | 12/1999 |
| WO | WO 00/03756 | 1/2000 |
| WO | WO 01/03762 | 1/2001 |
| WO | WO 01/07101 | 2/2001 |
| WO | WO 0107101 A1 * | 2/2001 |
| WO | WO 03/057060 | 7/2003 |
| WO | WO 03/105671 | 12/2003 |
| WO | WO 2004/064891 | 8/2004 |
| WO | WO 2004/096338 | 11/2004 |
| WO | WO 2006/002199 | 1/2006 |
| WO | WO 2006/058434 | 6/2006 |
| WO | WO 2006/122243 | 11/2006 |
| WO | PCT/US2007/067237 | 4/2007 |
| WO | PCT/US2007/067238 | 4/2007 |
| WO | PCT/US2007/067239 | 4/2007 |
| WO | PCT/US2007/067240 | 4/2007 |
| WO | PCT/US2007/067242 | 4/2007 |
| WO | PCT/US2007/067243 | 4/2007 |
| WO | PCT/US2007/067244 | 4/2007 |
| WO | WO 2007/124495 | 11/2007 |
| WO | WO 2007/124496 | 11/2007 |
| WO | WO 2007/124497 | 11/2007 |
| WO | WO 2007/124499 | 11/2007 |
| WO | WO 2007/124500 | 11/2007 |
| WO | WO 2007/124501 | 11/2007 |
| WO | WO 2007/143288 | 12/2007 |

OTHER PUBLICATIONS

U.S. Appl. No. 11/738,382, filed Apr. 20, 2007, Von Oepen.
U.S. Appl. No. 11/738,378, filed Apr. 20, 2007, Von Oepen.
U.S. Appl. No. 11/738,372, filed Apr. 20, 2007, Yribarren.
U.S. Appl. No. 11/738,386, filed Apr. 20, 2007, Von Oepen.
U.S. Appl. No. 60/793,781, filed Apr. 21, 2006, Von Oepen.
U.S. Appl. No. 11/738,382, filed Aug. 11, 2008, Office Action.
U.S. Appl. No. 11/738,372, filed Jun. 9, 2008, Office Action.
U.S. Appl. No. 11/738,372, filed Sep. 15, 2008, Office Action.
U.S. Appl. No. 11/738,382, filed Feb. 20, 2009, Office Action.
U.S. Appl. No. 11/738,372, filed Mar. 30, 2009, Office Action.
U.S. Appl. No. 11/738,382, filed Aug. 20, 2009, Office Action.
U.S. Appl. No. 11/738,378, filed Sep. 2, 2009, Office Action.
U.S. Appl. No. 11/738,372, filed Nov. 6, 2009, Office Action.
U.S. Appl. No. 11/738,382, filed Mar. 5, 2012, Notice of Allowance.
U.S. Appl. No. 11/738,384, filed Mar. 31, 2011, Notice of Allowance.
U.S. Appl. No. 11/738,384, filed Jul. 20, 2011, Issue Notification.
U.S. Appl. No. 11/738,386, filed Sep. 28, 2009, Office Action.
U.S. Appl. No. 11/738,386, filed Apr. 22, 2010, Office Action.
U.S. Appl. No. 11/738,372, filed May 12, 2010, Office Action.
U.S. Appl. No. 11/738,378, filed May 12, 2010, Office Action.
U.S. Appl. No. 11/738,382, filed Apr. 20, 2010, Office Action.
U.S. Appl. No. 11/738,384, filed Mar. 2, 2010, Office Action.
U.S. Appl. No. 11/738,384, filed May 14, 2010, Office Action.

U.S. Appl. No. 11/738,372, filed Jul. 26, 2010, Office Action.
U.S. Appl. No. 11/738,378, filed Aug. 17, 2010, Office Action.
U.S. Appl. No. 11/738,386, filed Nov. 8, 2011, Office Action.
U.S. Appl. No. 11/738,384, filed Oct. 27, 2010, Office Action.
U.S. Appl. No. 11/738,378, filed Oct. 4, 2010, Advisory Action.
U.S. Appl. No. 11/738,378, filed Nov. 26, 2010, Office Action.
U.S. Appl. No. 11/738,372, filed Dec. 23, 2010, Notice of Allowance.
U.S. Appl. No. 11/738,382, filed Jan. 4, 2008, Office Action.
U.S. Appl. No. 11/738,386, mailed Jun. 21, 2012, OA.
U.S. Appl. No. 11/738,382, mailed Jun. 6, 2012, IN.

* cited by examiner

*Fig. 6*

SUPPORT CATHETER

CROSS-REFERENCE TO RELATED APPLICATIONS

This application claims the benefit of the U.S. Provisional Patent Application No. 60/793,781, filed Apr. 21, 2006, and entitled "Medical Devices," which is incorporated herein by reference in its entirety.

BACKGROUND OF THE INVENTION

I. Field of the Invention

The present invention generally relates to the field of medical devices. More specifically, the present invention relates to support catheters that can be manipulated to track through vessels of the body as well as through obstructions in such vessels.

II. Related Technology

The use of intravascular devices to treat cardiovascular diseases is well known in the field of medicine. The need for a greater variety of devices to address different types of circumstances has grown tremendously as the techniques for using intravascular devices has progressed. One type of intravascular device is a catheter. Typically, an intravascular catheter is delivered into the body by first using a support catheter that can be routed through the proper vessels in the body's vascular network in order to arrive at a site in need of a diagnostic or therapeutic technique.

Previously, support catheters have been relatively simple and have been made of biocompatible plastics forming a shaft with a hollow internal lumen. The shaft is generally formed by one or more concentric tubes that are congruent to each other, where one tube typically provides support and the other tube(s) provide biocompatibility. Additionally, most support catheters include a hub that is connected to a proximal end of the shaft in order to provide a mechanism for connecting another device, such as an inflation device or syringe, and in order to provide a means to direct a subsequent guidewire through the support catheter into the vessel to the desired location for treatment or diagnostics. Usually, the tip of the support catheter is flexible and/or shaped in order to allow for deployment and placement in the tortuous vasculature network.

In order for a medical professional to insert the catheter into the proper location in the vessel, longitudinal and rotational forces applied to the support catheter must be translated to the distal end on the tip of the support catheter. This enables the medical professional to maneuver the distal end of the support catheter through various bends, junctions, or features of vessels in the vasculature. The tip of the support catheter can be soft and flexible to prevent damage to the vasculature as the support catheter is pushed or advanced therethrough. As such, the existing support catheters are stiff enough to be advanced through a blood vessel, yet include the flexible tip to aid with guiding the catheter through or around various bends or junctions.

The treatment of chronic total occlusions ("CTOs") has raised even further challenges to accessing both sides of the CTO. A CTO is a chronic problem that developed into a total obstruction or blockage in a vessel. The composition of a CTO may be classified as hard plaque, soft plaque or a mixture of the two. Percutaneous intervention is a minimally invasive way to treat vessels having CTOs and is accomplished with conventional guidewire techniques, e.g., slowly advancing the guidewire through the CTO to obtain the desired access to deploy balloon, stents, or other medical devices. As set forth above, catheters often are used to provide support to the guidewire.

In many cases, there is a cap with a calcified lesion at the proximal side of the occlusion (the "proximal cap"), where the blood flow is obstructed at the occlusion. It can be very difficult to advance a guidewire through this proximal cap to penetrate the CTO unless one can maneuver a guidewire or device through it. There are micro channels that run through the CTO. These micro channels may aid the medical professional in being able to maneuver a guidewire through a CTO. Crossing the proximal cap with a guidewire or other device or exploiting the micro channels, is a goal in recanalizing a vessel since it facilitates clearing the occlusion from the vessel.

It would be advantageous to have a support catheter that has the properties of flexibility and rigidity that further aid in maneuvering a guidewire through the CTO. More particularly, it would be advantageous to have a support catheter that can track to the site of a vessel occlusion, such as a CTO, and provide sufficient support to aid the guidewire to cross the occlusion.

BRIEF SUMMARY OF THE INVENTION

A support catheter is disclosed. The support catheter can be used to track to the site of a vessel occlusion, such as a chronic total occlusion, and provide sufficient support to aid a guidewire in crossing the occlusion. The support catheter comprises a catheter body having a length and at least a first portion and a second portion, each of the first portion and the second portion being formed of a material of differing hardness levels. The support catheter further comprises a supporting structure operatively associated with the first portion, the supporting structure in combination with the material forming the first portion varying the stiffness of the first portion relative to the second portion and varying the stiffness of the catheter body along its length.

In some configurations, the supporting structure comprises a separate coil mounted to the at least a portion of the length of the catheter body. In some configurations, the supporting structure comprises at least one groove formed in the at least a portion of the length of the catheter body. In some configurations, the supporting structure comprises at least one stiffening portion and at least one flexing portion.

According to some configurations, the supporting structure is formed over the at least a portion of the length and has a first flexibility characteristic different from at least another portion of the length of the catheter body. In some configurations, the supporting structure comprises at least one recess formed in the at least a portion of the length.

In certain configurations, the catheter further comprises a jacket layer disposed upon the catheter body, the jacket layer comprising at least two separate portions, each portion being formed from a different material, each having a different hardness level. In some configurations, the supporting structure comprises an inner liner formed on an inner wall of the catheter body, the inner liner comprising at least two separate portions, each portion being formed from a different material, each having a different hardness level.

According to other configurations, the support catheter comprising a catheter body having a length and a supporting structure operatively associated with the catheter body, wherein the supporting structure comprises at least one stiffening section and at least one flexing section, the combination of the at least one stiffening section and at least one flexing section varying a stiffness of the catheter body along the length. In some configurations, the at least one flexing section comprises a plurality of coil sections, each coil section being a coil embedded in the catheter body, and the at least one stiffening section comprises a plurality of ring sections, each ring section being a generally cylindrically-shaped tubular portion.

In some configurations, the coil is made from a metal, a shape memory material, or a polymer. In some configurations, the flexing section comprises a plurality of spaced apart recesses formed in a portion of the catheter body. In some configurations, the at least one flexing section comprises at least one groove formed in the catheter body. In some configurations, the catheter body further comprises at least two separate portions, each portion being formed from a different polymer, each having a different hardness level.

In certain configurations, the catheter further comprises a jacket layer disposed upon the catheter body, the jacket layer comprising at least two separate portions, each portion being formed from a different material, each having a different hardness level. In some configurations, the catheter further comprises an inner liner formed on an inner wall of the catheter body, the inner liner comprising at least two separate portions, each portion being formed from a different material, each having a different hardness level.

According to other configurations, a support catheter comprising a catheter body having a proximal end spaced apart from a distal end, a wall extending from the proximal end toward the distal end, and a plurality of recess formed in the wall of the catheter body, wherein the frequency of the plurality of recess varies from the proximal end toward the distal end. In some configurations, each of the plurality of recess comprises a generally I-shaped recess or a generally T-shaped recess. In some configurations, the catheter body comprises an inner surface, the inner surface being lined with a polymeric liner. In some of these configurations, the polymeric liner comprises at least two separate portions, each portion being formed from a different material, each having a different hardness level.

According to some configurations, the catheter body further comprises at least a first portion and a second portion, each of the first portion and the second portion having different hardness levels. In some configurations, each of the first portion and the second portion comprises a polymeric material. In some configurations, the catheter further comprises a jacket layer formed of at least two polymeric materials, each polymeric material having a different hardness level from the other polymeric materials.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings.

DETAILED DESCRIPTION

Reference will now be made to figures wherein like structures will be provided with like reference designations. It is understood that the drawings are diagrammatic and schematic representations of exemplary embodiments of the invention, and are not limiting of the present invention nor are they necessarily drawn to scale.

As described herein, the support catheter is employed to back up and support a guidewire and optionally assist in placing a guidewire within a body lumen of a patient, such as, but not limited to, the lumen of a coronary artery and through a blockage, such as a CTO within a coronary artery. For instance, the support catheter can be tracked over and provide support to a guidewire that is already placed in a body lumen. However, this description is exemplary only, and it should be appreciated that embodiments of the present catheter can be employed for multiple other purposes, including, but not limited to, the piercing of a blockage in a variety of body lumens, including the urinary tract, bile duct, esophagus and tracheo-bronchial tree, neurovascular, peripheral vascular, cardiac, and renal catheters, among others.

Generally, the present invention is related to support catheters. The support catheter provides support to a guidewire when additional support is needed, such as when the guidewire is to cross a chronic total occlusion ("CTO") or other vessel occlusion so that a medical professional can more quickly, easily and efficiently recanalize vessels that have occlusions or CTOs. The support catheter of the present invention provides optimized flexibility and support by varying the characteristics of the catheter in the axial direction based upon the particular procedural use of the support catheter. For instance, a support catheter for use in treating CTOs may be different than those used for other vessel occlusions or other medical procedures.

Figure 1A:
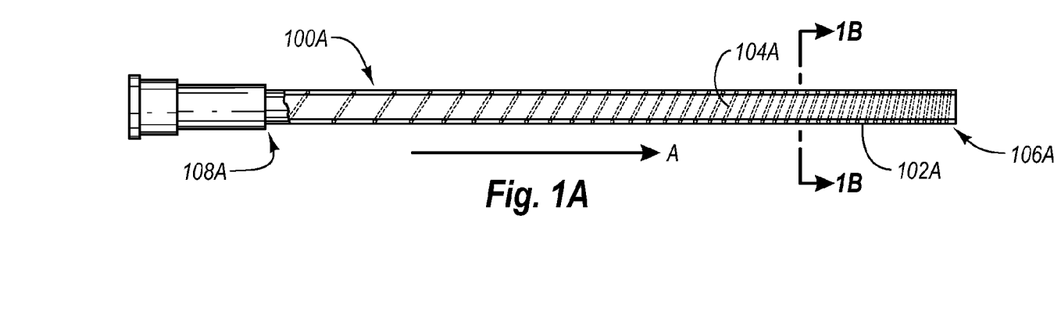
FIG. 1A illustrates a schematic side view of an embodiment of the support catheter according to the present invention.
Figure 1B:
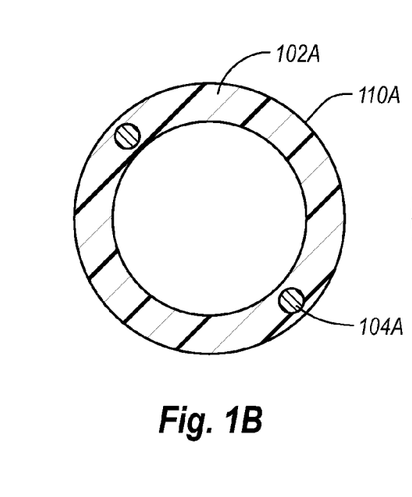
FIG. 1B illustrates a schematic cross-sectional view of the embodiment of the support catheter of FIG. 1A.

FIGS. 1A and 1B illustrate a schematic view of an embodiment of a support catheter 100A usable to aid a guidewire to cross a lesion or other obstruction, such as a CTO. As illustrated, the support catheter 100A includes a catheter body 102A and a catheter supporting structure or member 104A surrounding portions of the catheter body 102A and defining a profile or design on the support catheter. The catheter support member 104A can extend from a distal end or portion 106A to a proximal end or portion 108A of the catheter body 102A in a helical or spiral fashion. The catheter support member 104A has a varied pitch along the length of the catheter body 102A, the longitudinal axis of the catheter body 102A being the spiral axis of the catheter support member 104A. At the proximal end 108A of the catheter 100A, the pitch or distance between coils of the catheter support member 104A per unit length is the greatest, whereas at the distal end 102A of the catheter 100A, the pitch is the smallest. As shown in FIG. 1A, the pitch decreases in the direction of arrow A. With this configuration of support catheter 100A, the varied pitch results in a catheter that has excellent pushability, but has increased resistance to flexure where the pitch is greatest. To achieve different properties, however, the pitch may increase in the direction of arrow A, or vary in a more random manner over the length of the catheter. Further, varying the stiffness or hardness properties of the catheter support member 104A and/or the catheter body 102A can also result in increased or decreased flexibility when the pitch is smallest or when the pitch is greatest.

Figure 1C:
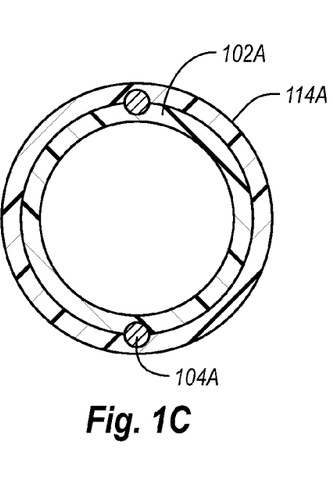
FIG. 1C illustrates a schematic cross-sectional view of an alternate embodiment of the support catheter of FIG. 1A.

With continued reference to FIGS. 1A and 1B, the catheter support member 104A is shown as being embedded within the catheter body 102A. For instance, the catheter support member 104A can be a metallic or polymeric coil that is formed in the wall 110A of the catheter body 102A during manufacture. For instance, during extrusion of the catheter body 102A, the catheter support member 104A can be positioned in the wall 110A. Alternatively, the catheter support member 104A can be embedded in an extrusion of the catheter body 102A and the catheter support member 104A and the catheter body 102A covered with a biocompatible polymer layer 114A, as illustrated in FIG. 1C. This may be facilitated by embedding the catheter support member 104A while the extrusion of the catheter body 102A has not set and shows viscoelastic characteristics. It will be understood that the catheter body 102A and the biocompatible layer 114A can be co-extruded with the catheter support member 104A disposed therebetween. Further, it will be understood that when the catheter body 102A and the catheter support member 104A are both fabricated from biocompatible materials, the biocompatible layer 114A can be omitted. This configuration provides an additional advantage of providing a threaded outer surface that is capable of screwing into a CTO lesion and therefore crossing the lesion or providing additional support.

Figure 1D:
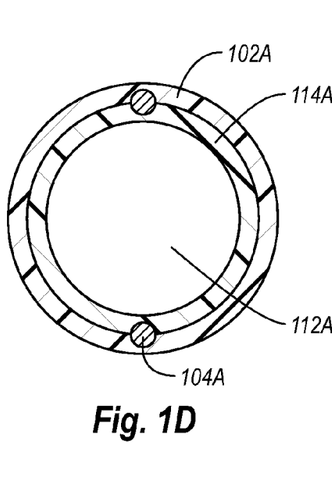
FIG. 1D illustrates a schematic cross-sectional view of an alternate embodiment of the support catheter of FIG. 1A.

In an alternative embodiment, as illustrated in FIG. 1D, an exposed support member 104A may be on the inside of the catheter body 102A, which would result in reduced surface contact with the guidewire and therefore improved trackability. In still another configuration, also shown in FIG. 1D, the catheter support member 104A, such as a metallic or polymeric coil, can be disposed around an interior lumen 112A of the catheter body 102A following or during extrusion of the catheter body 102A, the metallic or polymeric coil being subsequently covered (inside of the catheter body 102A) with a biocompatible polymer layer 114A, As with positioning or locating the catheter support member 102A upon the outer surface of the catheter body 104A, the catheter body 102A and the biocompatible layer 114A can be co-extruded with the catheter support member 104A disposed therebetween.

The catheter support member 104A can have various configurations, while providing the desired functionality. As described thus far, the catheter support member 104A is a separate structure that is mounted or operatively associated with the catheter body 102A. The catheter support member 104A can be a coil, wire, ribbon, or other similar structure, no matter the particular cross-sectional configuration of the coil, wire, ribbon, or other similar structure. Other suitable structures include one of, or a combination of a braid, zig-zag, spaced rings, wave or undulating structure.

Figure 1E:
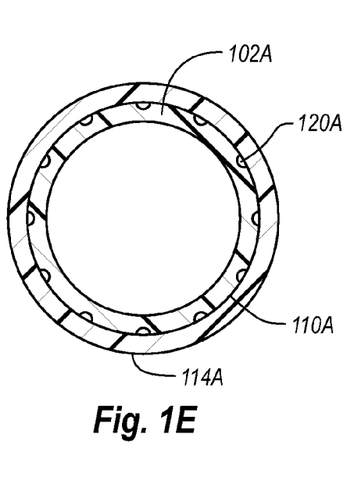
FIG. 1E illustrates a schematic cross-sectional view of an alternate embodiment of the support catheter of FIG. 1A.

In still another configuration, the functionality of the catheter support member 104A can be provided from the combination of structures formed in the catheter body 102A and a biocompatible or non-biocompatible layer disposed on the catheter body 102A. With reference to FIG. 1E, one or more grooves 120A can be formed in the wall 110A of catheter body 102A, those one or more grooves 120A having variable pitch in a similar manner and to provide a similar function to that described herein.

With the one or more grooves 120A, the biocompatible layer 114A can be formed on the surface of the wall 111A. Portions of the biocompatible layer 114A extend into and substantially or completely fill the one or more grooves 120A. A non-biocompatible layer can alternatively be disposed on the surface of wall 110A, so long as a biocompatible layer 114A is disposed upon this non-biocompatible layer. It is also possible to not cover or fill the grooves 120A and to use the grooves 120A as fluid transport lumens, for example, to flush saline or therapeutic agents from the proximal end 108A to the distal end 106A.

Depending upon the groove depth, groove spacing and width, the pitch of the grooves, and the characteristics of the material forming the catheter body 102A, the non-biocompatible layer, and/or the biocompatible layer 114A, the support catheter 100A can have varied stiffnesses and strengths.

Formation of the grooves 120A in the catheter body 102A can occur during and/or following extrusion of the catheter body 102A. For instance, an extrusion die (not shown) can include a tooth or other protrusion that forms the groove, with the extrusion die (not shown) either being stationary or rotating during the extrusion process. Alternatively, the groove(s) 120A can be formed through laser cutting, etching, or other manufacturing techniques known to those skilled in the art.

The catheter support member or supporting structure 104A or any supporting structure within the spirit of the invention is operatively associated with the catheter body 102A. Note that operatively associated means that the supporting structure 104A (or any supporting structure) may be mounted to the catheter body, embedded in the catheter body, lined on the catheter body, or that the supporting structure 104A (or any supporting structure) may comprise grooves formed in the catheter body 102A, may comprise a stiffening portion and/or a flexing portion, and/or may comprise a plurality of recess (or spaced-apart recess) formed in the catheter body. In addition to those already described, various embodiments and examples of each of these supporting structures will be set forth in detail below.

Another factor of variability with the support catheter 100A is that of hardness or durometer level of the materials used to form the support catheter 100A. That is, the catheter 100A also may have a hardness that may vary over its length. For example, the durometer level of catheter 100A may be the hardest at the proximal end 108A and gradually vary to the softest level at the distal end 106A (or vice versa). In other words, the durometer level of the catheter 100A decreases in the direction of arrow A (or vice versa), or varies in a more random manner over the length of the catheter 100A. Further, the hardness or durometer level of the biocompatible layer 114A and/or the non-biocompatible layer can be different from that of the catheter body 102A and also can optionally vary along the length of the catheter 100A. Stiffness also may be affected by varying the polymer crystallinity. For example, the hardness of the catheter body 102A may be varied by manufacturing the catheter body 102A with different materials such as various polymers, each having a different hardness level. Also, the direction of stress lines will impact the material stiffness, and may be affected by applying variable cooling of the material during the extrusion process.

Figure 2A:
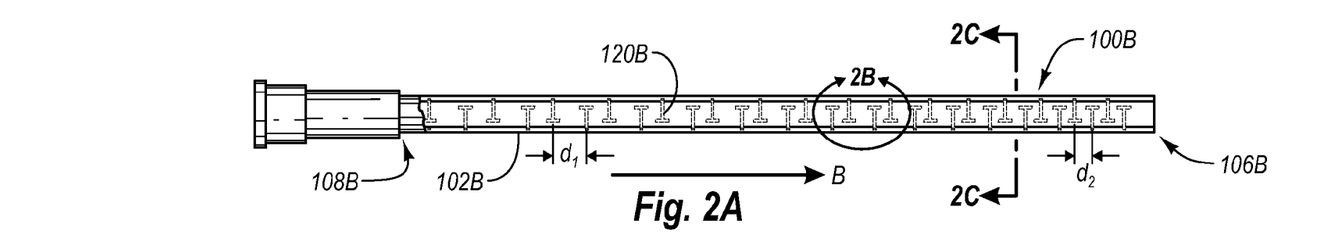
FIG. 2A illustrates a schematic side view of an alternate embodiment of the support catheter according to the present invention.
Figure 2B:
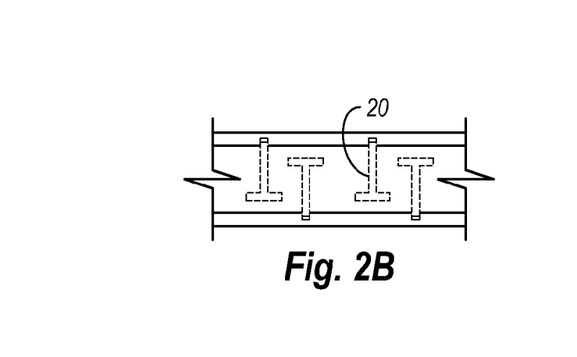
FIG. 2B illustrates an enlarged view of the I-Beam design shown of the support catheter of FIG. 2A.

FIGS. 2A and 2B illustrates a schematic side view of an alternate embodiment of the improved support catheter 100B according to the present invention. It will be understood that the description related to support catheter 100A can also apply to support catheter 100B, and vice versa.

As shown, support catheter 100B includes a catheter body 102B having a plurality of catheter support structures 104B in the form of I or T-shaped recesses 120B, although other configurations of the recesses are possible. Other recess shapes include, but are not limited to, U shapes, zig-zag shapes, and wave-like or undulating shapes. As with the configuration described with respect to FIG. 1E, the location, number, orientation, and configuration of the recesses 120B provides the functionality of the catheter support member to the support catheter 100B. An enlarged view of the design or profile of the catheter support structures 104B is shown in FIG. 2B.

With continued reference to FIG. 2A, the profile or frequency of the catheter support structures 104B is varied along the length of the catheter 100B. That is, at a proximal end or portion 108B of the catheter 100B, the frequency, density, or number of catheter support structures 104B per unit length is the smallest, whereas at a distal end or portion 106B of the catheter 100B, the frequency, density, or number of catheter support structures 104B per unit length is the greatest. Stated another way, adjacently positioned catheter support structures 104B near the proximal end 108A are spaced apart a distance $d_1$, while adjacently positioned catheter support structures 104B near the distal end 106A are spaced apart a distance $d_2$, $d_1$ being greater than $d_2$ in the illustrated configuration. Thus, as shown in FIG. 2A, the frequency of the catheter support structures 104B increases in the direction of arrow B. By varying the catheter support structures 104B and frequency or density across the length of the catheter 100B, the flexibility is varied. It is understood that in an alternate configuration, the configuration can be the opposite, i.e., the frequency of the catheter support structures 104B increases in the direction of arrow B.

Figure 2C:
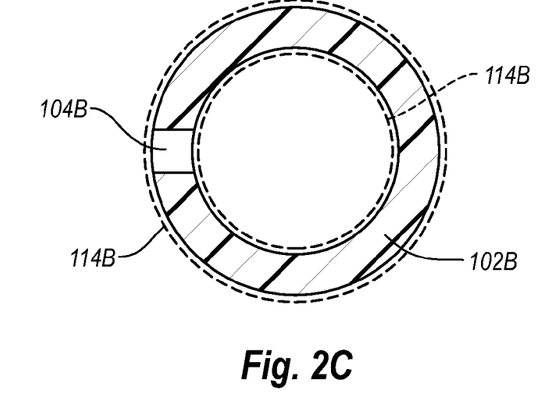
FIG. 2C illustrates a schematic cross-sectional view of an alternate embodiment of the support catheter of FIG. 2A.

In the illustrated configuration of support catheter 100B, and with reference to FIG. 2C, the recesses 120B or catheter support structures 104B pass through the wall 110B of the catheter body 104B. To create a fluid sealed structure, a biocompatible layer 114B can be disposed upon the surface of the catheter body 104B. This layer 114B can be disposed upon an outer surface or within the interior surface of the catheter body 104. A non-biocompatible layer can alternatively be disposed on the surface of wall 110A, so long as a biocompatible layer 114B is disposed upon this non-biocompatible layer.

With the improved support catheter 100B, an advantage is that there is an increase in torsional transmission, i.e., from the proximal end 108B to the distal end 106B of the catheter 100B through manipulation by a medical professional. To achieve different properties, however, the frequency or density may increase in the direction of arrow B, or vary in a more random manner over the length of the catheter 100B, as will be appreciated based upon the description herein and/or the knowledge of one skilled in the art.

Figure 3:
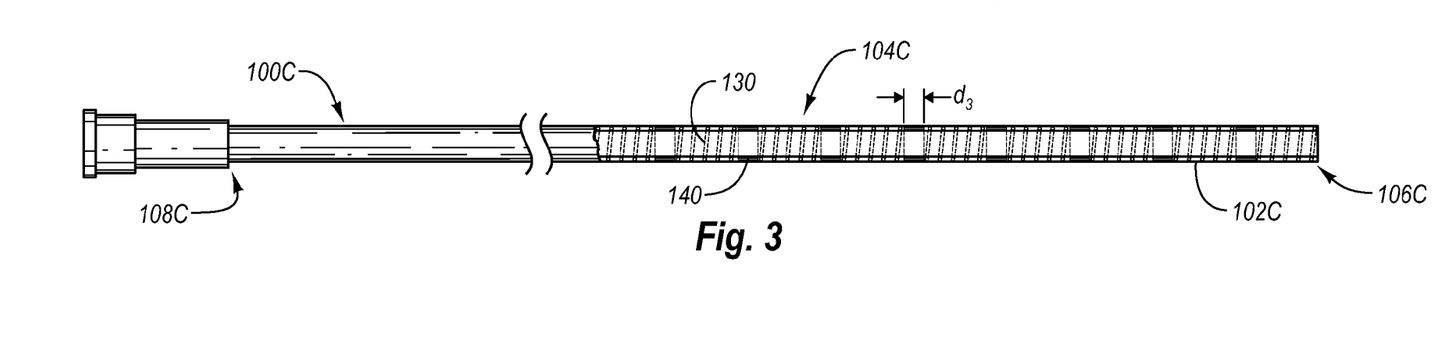
FIG. 3 illustrates a schematic side view of an alternate embodiment of the support catheter according to the present invention.

FIG. 3 illustrates a schematic side view of an alternate embodiment of the improved support catheter 100C, which includes a catheter body 102C and a supporting member or supporting structure 104C surrounding portions of the catheter body 102C. The catheter support member 104C can extend from a distal end or portion 106C to a proximal end or portion 108C of the catheter body 102C, but may include multiple distinct sections of catheter support member 104C that either maintain or provide stiffness or flexibility to the catheter 100C. As shown, catheter 100C of FIG. 3 includes a catheter body 102C and two distinct sections of catheter support member 104C, namely coil sections 130 that provide enhanced flexibility and ring sections 140 that provide catheter stiffness. As with the supporting member 104A of catheter 100A, the coil sections 140 are spirals of various pitches (which may include uniform pitch), designed to provide optimum torsion and flexibility. The ring sections 140 link the coil sections 130 and can be cylindrical tubing sections with no breaks in the wall. These ring sections 140 offer increased stability to the supporting member 104C and help to modulate the torsional transmission of the overall structure of the catheter 100C. Further, the length or width $d_3$ of each ring section 140 may be varied as necessary to provide optimum flexibility of the catheter 100C. The coil sections 130 may run along the catheter body 102C with the ring sections 140 interspersed between the coil sections 140 at regular intervals, as shown in FIG. 3, or may be spaced in a more random pattern, or in a pattern that increases in frequency or decreases in frequency along the length of the catheter 100C.

As shown in FIG. 3, the coil sections 130 and ring sections 140 of the supporting member 104C are embedded within catheter body 102C. As shown and described above with respect to catheter 100A, however, other methods of manufacture are possible. For example, coil sections 130 and ring sections 140 may be embedded in a still warm extrusion of the catheter body 102C, or co-extruded with the catheter support member 104C disposed between a biocompatible polymer layer and the catheter body 102C. In still another configuration, the coil sections 130 can receive or be formed with the catheter support member 104C, while the ring sections 140 do not receive or are not formed with the catheter support member 104C. Stated another way, the ring sections 140 are formed from the catheter body 102C, while the coil sections 130 receive or are formed with the catheter support members or structures 104C.

Furthermore, the alternate configurations set forth and described above with respect to catheter 100A also are possible with the multiple distinct sections of catheter support member 104C of catheter 100C. Also note that catheter 100C is an example of how a catheter of the present invention can include catheter support structures 104C that comprise both stiffening sections and flexing sections. With catheter 100C, the stiffening sections comprise the ring sections 140, whereas the flexing sections comprise the coil sections 130.

Figure 4:
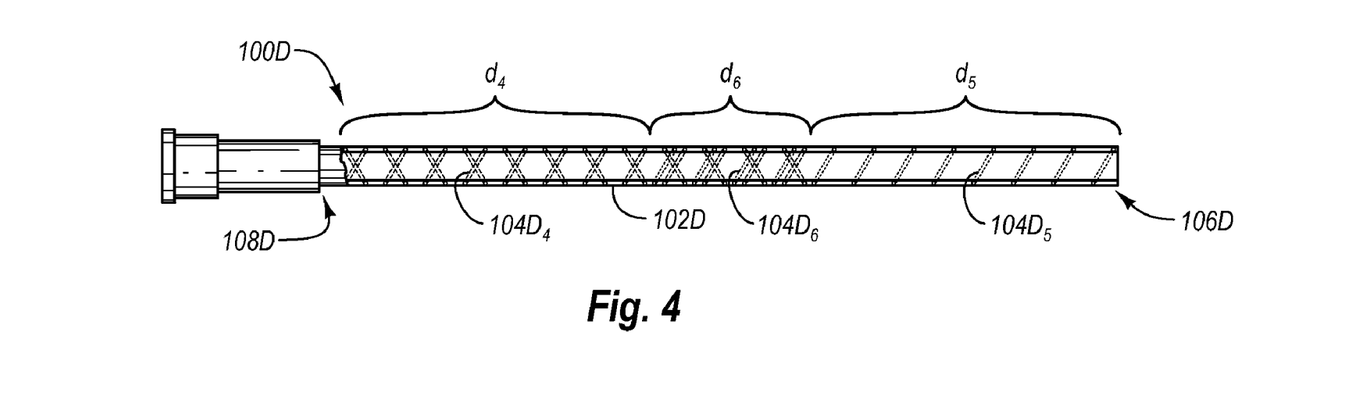
FIG. 4 illustrates a schematic side view of an alternate embodiment of the support catheter according to the present invention.

FIG. 4 illustrates a schematic view of another embodiment of a support catheter 100D usable to aid a guidewire to cross a lesion or other obstruction, such as a CTO. As illustrated, the support catheter 100D includes a catheter body 102D having three portions $d_4$, $d_5$ and $d_6$, each of which has different catheter supporting structures or members. Portion $d_4$ is situated closest the proximal end 108D of the support catheter 100D and has a braided supporting structure or member $104D_4$. Portion $d_5$ is situated closest the distal end 106D of the support catheter and has coils as the supporting structure or member $104D_5$, which are similar to the coils 104A. The coils $104D_5$ are shown having a uniform pitch, but to obtain different properties, may increase or decrease over the length of the portion $d_5$, or vary in a more random manner over the length of the portion $d_5$.

Portion $d_6$ is situated in between the portion $d_4$ and $d_5$ and is comprised of an combination of supporting structure $104D_6$, which consists of an overlapped portion of the braided supporting structure $104D_4$ and the coils $104D_5$. With this configuration of the support catheter 100D, each portion $d_4$, $d_5$ and $d_6$ provides different stiffness and torque transmission characteristics to the catheter body 102D. To achieve different properties, any variations as discussed herein may be made to catheter 100D. For example, the make up of the portions $d_4$, $d_5$ and $d_6$ may vary, or as described, the pitch of the coils on portion $d_5$ may vary. Similarly, note that it is not necessary that the supporting structures $104D_4$ and the coils $104D_5$ overlap.

Figure 5:
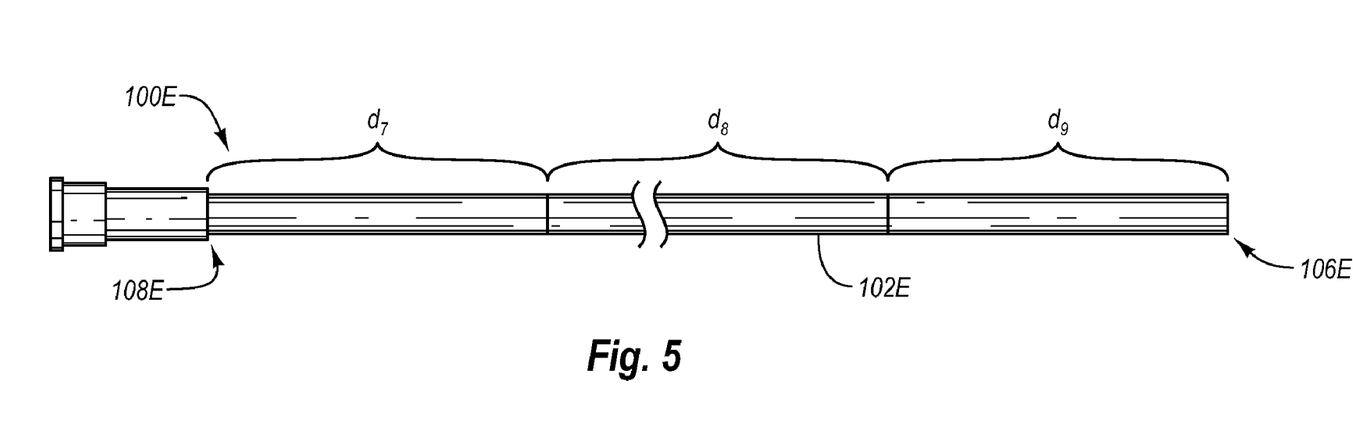
FIG. 5 illustrates a schematic side view of an alternate embodiment of the support catheter according to the present invention.

FIG. 5 illustrates a schematic view of another embodiment of a support catheter 100E usable to aid a guidewire to cross a lesion or other obstruction, such as a CTO. As illustrated, the support catheter 100E includes a catheter body 102E having three distinct portions $d_7$, $d_8$ and $d_9$ over the length of the catheter body 102E. As with catheter 100D, catheter 100E provides a catheter in which each portion $d_7$, $d_8$ and $d_9$ can provide different stiffness and/or torque transmission characteristics to the catheter body 102E by having or utilizing different catheter supporting structures. For example and for illustrative purposes, portion $d_7$ may utilize supporting structures 104A, portion $d_8$ may utilize supporting structures 104B, and portion $d_9$ may utilize supporting structures $104D_4$. Similarly, portion $d_7$ may be a stiffening portion, portion $d_8$ may be a flexing portion, and portion $d_9$ may vary in hardness level, or any combination thereof In such an embodiment, the flexing portion may comprise coils embedded in the catheter body, and the stiffening portion comprises braid section being embedded in the catheter body.

In the embodiments described above, the support members 104A, 104B, 104C, $104D_4$, $104D_5$, $104D_4$ or $104D_6$ are manufactured from a metal such as stainless steel for strength characteristics, but may be fabricated from any material. Instead of stainless steel, a shape memory alloy such as Nitinol may be used, but plastic materials such as polyamide or nylon also may be utilized. Further, the materials forming the catheter support member 104A, 104B, 104C, $104D_4$, $104D_5$, $104D_4$ or $104D_6$ can be varied to provide differences in the stiffness and operable characteristics of the support catheter 100A, 100B, 100C, 100D or 100E, respectively. For instance, the catheter support member 104A, 104B, 104C, $104D_4$, $104D_5$, $104D_4$ or $104D_6$ can be fabricated from a metal, a metal alloy, a polymer, a synthetic material, a natural material, combinations thereof, or other materials that provide the desired stiffness and/or biocompatibility. Suitable metals include stainless steel, Nitinol, elgiloy, and cobalt chromium. Suitable polymers include PTFE, ePTFE, PEEK, polyimide, and Pebax.

Further, if the support member 104A, 104B, 104C, $104D_4$, $104D_5$, $104D_4$ or $104D_6$ is made of metal, it is desirable not to have the support member contact the guidewire. For example, the support member 104A, 104B, 104C, $104D_4$, $104D_5$, $104D_4$ or $104D_6$ may be embedded in a polymeric material or the inner surface of the support member may be lined with a polymeric material. A polymeric material that would be suitable for this purpose is high density polyethylene (HDPE) due to its low friction surface characteristics. Other suitable materials include polyimide, PEEK, polytetrafluorethylene, polyvinylidene fluoride, and polyamide.

Figure 6:
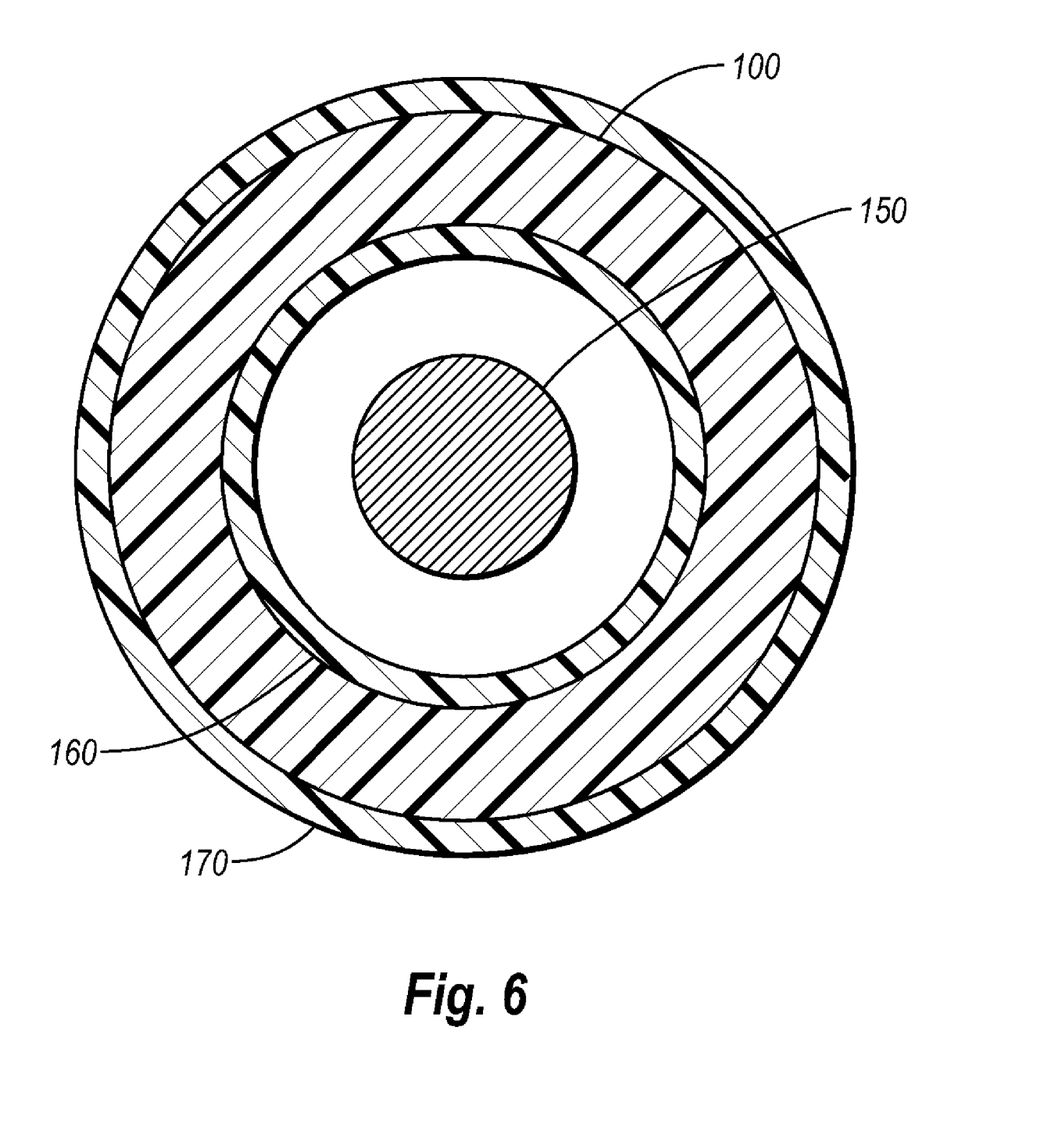
FIG. 6 shows a schematic cross-sectional view of a representative support catheter according to the present invention in cooperation with a guidewire.

FIG. 6 shows a schematic cross-sectional view of the improved support catheter 100 according to the present invention in cooperation with a guidewire 150. As shown in FIG. 6, improved support catheter 100 represents any of the above embodiments 100A, 100B, 100C, 100D or 100E. As described above, the improved support catheter 100 has an inner lining 160 coating the inner surface of the catheter 100. Also as described, this inner lining 160 may be a polymeric material 160 such as HDPE. Further, improved support catheter 100 has an outer jacket layer or classic jacketing 170 extruded over the outer surface of the catheter 100. This jacket layer 170 may be made of a biocompatible polymer. Other suitable materials include polyimide, PEEK, polytetrafluorethylene, polyvinylidene fluoride, and polyamide. Lastly, FIG. 6 shows a guidewire 150 at the center opening of catheter 100.

It is important to note that support catheters having any combination of the supporting members of structures 104A, 104B, 104C, $104D_4$, $104D_5$, $104D_4$ and $104D_6$ and/or wherein the hardness level is varied are contemplated. For example, any of the catheters 100A, 100B, 100C, 100D or 100E disclosed herein, or variation thereof may be constructed with a catheter body 102A, 102B, 102C, 102D or 102E with different materials such as various polymers, each having a different hardness level. In this way, catheter 100A, 100B, 100C, 100D or 100E also will have a hardness level that will vary over its length. In addition to manufacturing the catheter body with polymers of varying hardness levels, it also is possible to construct a catheter with, for example, an inner lining 160 or a jacket layer 170 with polymers of varying hardness levels in the same manner, i.e., by constructing the inner lining 160 and/or the jacket layer 170 with different materials such as various polymers, each having a different hardness level.

Accordingly, as the improved support catheter 100 of the present invention is designed to be used for, among other applications, crossing a CTO or other vessel occlusion, but also for advancing over a guidewire 150, a metallic tip attached to the distal end of each catheter is beneficial. Metallic tips that would work well with the improved support catheter 100 of the present invention are disclosed in commonly-assigned U.S. patent application Ser. No. 11/683,997, entitled "Flexible Catheter Tip Having A Shaped Head," filed on Mar. 8, 2007, which is hereby incorporated by reference in its entirety.

By advancing the improved support catheter 100 of the present invention, the vessel wherein the CTO lies can be recanalized, i.e., the lumen size within the CTO can be increased. Then, by retracting the support catheter 100 from the guidewire 150, a balloon catheter and/or stent system may be tracked into the widened lesion lumen, and/or deployed to open the CTO.

The present invention may be embodied in other specific forms without departing from its spirit or essential characteristics. For example, each of the embodiments of the improved support catheter 100 of the present invention may be used with a rapid exchange (RX) catheter as well as an over the wire (OTW) catheter without departing from the intent of the invention. The described embodiments are to be considered in all respects only as illustrative and not restrictive. The scope of the invention is, therefore, indicated by the appended claims rather than by the foregoing description.

What is claimed is:

1. A support catheter comprising:
   a catheter body having a length extending from a proximal end to a distal end and having a plurality of first portions and a plurality of second portions disposed in alternating fashion from the distal end toward the proximal end, the first portions and the second portions having differing stiffnesses, with a wall of the second portions having a generally uniform cross-section; and
   a first supporting structure operatively associated with each of the first portions, the first supporting structure including a metallic or polymeric support member and extending from a first portion proximal end to a first portion distal end of the first portion, the first support structure being helically disposed on the first portion and having a variable helical pitch from the first portion proximal end to the first portion distal end so as to impart a stiffness to the first portion different than the stiffness presented by an adjacently positioned second portion of the plurality of second portions, and a second supporting structure operatively associated with each of the second portions, the second supporting structure including a cylindrically-shaped tubular ring portion extending from a second portion proximal end to a second portion distal end, the tubular ring portion being disposed on the second portion and having a wall with no breaks from the second portion proximal end to the second portion distal end so as to impart a stiffness to the second portion different than the stiffness presented by an adjacently positioned first portion of the plurality of first portions, the first and second supporting structures in combination with the material forming the plurality of first portions and the plurality of second portions varying the stiffness of the first portions relative to the second portions and varying the stiffness of the catheter body along its length from the proximal end to the distal end.

2. The support catheter as recited in claim 1, wherein the first supporting structure comprises a separate coil mounted to the first portion.

3. The support catheter as recited in claim 1, wherein the first supporting structure further comprises at least one groove formed in the first portion and adapted to receive the metallic or polymeric support member.

4. The support catheter as recited in claim 1, wherein the catheter further comprises a jacket layer disposed upon the catheter body, the jacket layer comprising at least two separate jacket layer portions, each jacket layer portion being formed from a different material, each material having a different hardness level.

5. The support catheter as recited in claim 1, further comprising an inner liner formed on an inner wall of the catheter body, the inner liner comprising at least two separate portions, each inner layer portion being formed from a different material, each material having a different hardness level.

6. A support catheter comprising:
a catheter body having a length, a proximal end and a distal end; and
a supporting structure operatively associated with the catheter body and extending from and varying in stiffness from the proximal end to the distal end, the supporting structure comprises a plurality of stiffening sections including a plurality of un-slotted ring sections, each ring section being a generally cylindrically-shaped, tubular portion having a wall with no breaks from a proximal end to a distal end of each stiffening section and a plurality of separate flexing sections including a plurality of coil sections adjacent one or more of the stiffening sections, each coil section being a coil and each stiffening section being a tubular member embedded in the catheter body, the combination of the at least one stiffening section and at least one flexing section varying a stiffness of the catheter body along the length.

7. The support catheter as recited in claim 6, wherein:
at least one of the plurality of stiffening sections comprises a braid section, the braid section being embedded in the catheter body.

8. The support catheter as recited in claim 7, wherein the coil is made from a metal, a shape memory material, or a polymer.

9. The support catheter as recited in claim 6, wherein the at least one flexing section further comprises a plurality of spaced apart recesses formed in a portion of the catheter body.

10. The support catheter as recited in claim 6, wherein the at least one flexing section further comprises at least one groove formed in the catheter body.

11. The support catheter as recited in claim 6, wherein the catheter body further comprises at least two separate portions, each portion being formed from a different polymer, each polymer having a different hardness level.

12. The support catheter as recited in claim 6, wherein the catheter further comprises a jacket layer disposed upon the catheter body, the jacket layer comprising at least two separate portions, each portion being formed from a different material, each material having a different hardness level.

13. The support catheter as recited in claim 6, further comprising an inner liner formed on an inner wall of the catheter body, the inner liner comprising at least two separate portions, each portion being formed from a different material, each material having a different hardness level.

14. A support catheter comprising:
a catheter body having a proximal end spaced apart from a distal end, a wall extending from the proximal end toward the distal end, and a length extending from the proximal end to the distal end; and
a plurality of generally T-shaped recesses formed in the wall of the catheter body with each T-shaped recess including a vertical portion having a first end and a second and a horizontal portion coupled to the second end of the vertical portion, adjacently positioned T-shaped recesses disposed along the length of the catheter body alternating in orientation from upright configuration to and from an inverted configuration and extending transversely across the longitudinal axis of the catheter body with adjacent T-shaped recesses being arranged such that the horizontal portion of a first T-shaped recess is disposed adjacent to the first end of the vertical portion of a second T-shaped recess and such that the horizontal portion of the second T-shaped recess is disposed adjacent to the first end of the first T-shaped recess, wherein the frequency of the plurality of recesses varies from the proximal end toward the distal end, the generally T-shaped recesses being configured to provide variable stiffness to the catheter body in at least two dimensions from the proximal end to the distal end.

15. The support catheter as recited in claim 14, wherein the catheter body comprises an inner surface, the inner surface being lined with a polymeric liner.

16. The support catheter as recited in claim 14, wherein the polymeric liner comprises at least two separate portions, each portion being formed from a different material, each material having a different hardness level.

17. The support catheter as recited in claim 14, wherein the catheter body further comprises at least a first portion and a second portion, each of the first portion and the second portion having different hardness levels.

18. The support catheter as recited in claim 17, wherein each of the first portion and the second portion comprises a polymeric material.

19. The support catheter as recited in claim 14, wherein the catheter further comprises a jacket layer formed of at least two polymeric materials, each polymeric material having a different hardness level from the other polymeric materials.

* * * * *